United States Patent
Donndelinger

(10) Patent No.: US 8,084,257 B2
(45) Date of Patent: Dec. 27, 2011

(54) METHODS FOR SORTING DIMORPHIC DAUGHTER CELLS

(76) Inventor: Thomas M. Donndelinger, Nampa, ID (US)

( * ) Notice: Subject to any disclaimer, the term of this patent is extended or adjusted under 35 U.S.C. 154(b) by 761 days.

(21) Appl. No.: 11/676,143

(22) Filed: Feb. 16, 2007

(65) Prior Publication Data

US 2008/0199954 A1    Aug. 21, 2008

(51) Int. Cl.
*C12N 5/00* (2006.01)
(52) U.S. Cl. ............... 435/376; 435/40.51; 435/325; 435/347; 435/289.1; 436/63; 436/164
(58) Field of Classification Search ............ 435/1.1, 435/2, 3, 6, 7.2, 7.92, 40.51, 40.52, 325, 435/347, 376, 287.2, 289.1; 436/63, 172, 436/164; 422/68.1, 73, 82.05, 101
See application file for complete search history.

(56) References Cited

U.S. PATENT DOCUMENTS

| | | | | |
|---|---|---|---|---|
| 6,620,591 B1 * | 9/2003 | Dunlay et al. | ............. | 435/7.2 |
| 2003/0124505 A1 * | 7/2003 | Jain et al. | ............. | 435/4 |

OTHER PUBLICATIONS

Kolas et al., Mutant meiotic chromosome core components in mice can cause apparent sexual dimorphic endpoints at prophase or X-Y defective male-specific sterility. Chromosoma, (Jul. 2005) vol. 114, No. 2, pp. 92-102.*

* cited by examiner

*Primary Examiner* — Gail R Gabel
(74) *Attorney, Agent, or Firm* — Kirton & McConkie; Evan R. Witt

(57) ABSTRACT

This invention relates to methods for distinguishing and sorting cells. In particular it includes methods for distinguishing and sorting post-mitotic and post-meiotic daughter cells into two classes according to differential cellular features. Labeling, tagging, or marking of the cells' chromatin proteins, RNA, or DNA may assist in distinguishing the daughter cells. In some embodiments, two cell classes may be studied and the cells' proteins, glycoproteins, and RNA may be identified and subset. Information from these subsets may then be used to distinguish and sort the two classes of cells from similar tissues according to protein, glycoprotein, and RNA makeup.

16 Claims, 8 Drawing Sheets

Fig. 1

METHODS FOR SORTING DIMORPHIC DAUGHTER CELLS

BACKGROUND OF THE INVENTION

This application relates generally to methods for distinguishing and sorting cells. In particular, this application relates to methods for differentiating post-mitotic (or post meiotic) eukaryotic and prokaryotic daughter cells due to differences in the cells' DNA, RNA, chromatin associated proteins, or other distinguishable cellular features. The cells may then be sorted according to the differential cellular features.

The Applicant has invented tissue preparation compositions and methods that dramatically improve visualization of cellular and intracellular morphology and function, including evaluation of differentials in post-mitotic cell pairs; evaluation of differences in chromosomes during mitosis; improved identification of detailed histochemical, proteomic, RNA and enzymatic features of cellular organelles, such as mitochondria and the nucleus; evaluation of differential viral infections; and improved cancer diagnosis and gradation. Features of the tissue preparation compositions and methods are disclosed in U.S. patent application Ser. No. 11/400,468 filed on Apr. 17, 2006 entitled "Compositions and Methods for Preparing Specimens for Microscopic Analysis," the entire disclosure of which is incorporated herein by reference.

The foregoing patent application includes examples and photomicrographs that illustrate differential staining of post-mitotic cell pairs. Such photomicrographs have led the Applicant to discover, contrary to the generally accepted dogma, that post-mitotic eukaryotic daughter cells vary due to differences in the cells' chromatin. In order to understand these differences, this application provides a brief explanation of chromatin.

To avoid being severely tangled or broken, DNA is packaged and wound in a complex that contains histones and nonhistone proteins. This complex, called chromatin, is generally found in the nucleus of eukaryotic cells and is the fundamental packaging unit from which chromosomes are made. Within a cell's chromatin, DNA is wound around a group of histones, known as the octomeric core, or octomer, and forms complexes known as nucleosomes, which are responsible for the "beads on a string" appearance of chromatin frequently observed in electron micrographs.

Histones are relatively small proteins with a very high proportion of positively charged amino acids (lysine and arginine) near their N-terminal end. The positive charge of these amino acids may help the highly negatively charged DNA bind tightly to histones in the octomer. The octomer generally comprises eight nucleosomal histones, or two units of each of the following histones: H2A, H2B, H3, and H4. Nearly two full turns of DNA are wound (83 nucleotide pairs per turn) around each octomer to form a nucleosome. Additionally, histone H1 binding (with multiple other factors) between nucleosomes increases the density of the DNA in chromatin. Chromatin may also contain other proteins, including the high mobility group ("HMG") chromosomal proteins HMG 14 and HMG 17 that may be bound to nucleosomes.

Further, the proteins found in the chromatin (e.g., histone H2A, H2B, H3, and H4, HMG 14, HMG 17, and H1) ("chromatin proteins") may also be modified. In some cases, various amino acids of the proteins may be phosphorylated, methylated, acetylated, and in some may be ribosylated or sumoylated. For example, histone H4 may be acetylated at lysine 16, lysine 8, or histone 1 may be phosphorylated. These protein modifications may also vary between daughter cells.

The Applicant has discovered that although two post-mitotic daughter cells have originated from the same cell division and have identical DNA (or nearly identical DNA as in differential DNA methylation), the two post-mitotic daughter cells are dimorphic, or asymmetrical, and can be sorted into two classes according to differences in the cells' chromatin, proteome, glycoproteome, RNA, DNA methylation, or other distinguishable cellular feature. In particular, one type of cell, which may be called class 0 for ease, seems to have chromatin that is lightly clumped in the periphery and finely divided in the center. Chromatin from these class 0 cells tends to stain lightly, as compared to the other class of cells. Additionally, the nucleolus in these cells tends to be centrally-located. The second class, which may be called class 1 for ease, has chromatin that is more densely clumped at the periphery with larger dense clumps in the inner portion and tends to stain darker than the class 0 cells. It is presumed that, in some respects, the differential staining exhibited in the two classes of cells is due to differential modification of histones.

Because histone proteins may be modified, and because the two classes of daughter cells generated from a cell division may contain differential modifications of histone proteins, the DNA in the two daughter cells may be differentially bound in chromatin. This difference in genome packaging may influence expression and activity of the packaged DNA, and as a result, influence the RNA, proteins, and glycoproteins that a cell produces, as well as the functions of a cell. For example, class 0 cells seem to express more genes than do class 1 cells. Because class 0 and class 1 cells express different numbers of genes, they ultimately express a different number, and likely type, of proteins.

Another nonbinding theory that may be used to explain dimorphic chromatin and other differences found in the two classes of cells is that epigenetic differences may be due to asymmetric methylation of the duplicated DNA that is found in daughter cells. The most common eukaryotic DNA modification is methylation of cytosine at position 5 ("m5C"). In animals, cytosine residues at CpG dinulceotides are often the preferred targets for DNA methylation, while methylation at CpG, CpN, and CpNpG sequences is common in plants. Often, methylation of the CpG, CpN, and CpNpG sites between parent and daughter DNA is not completely symmetrical. This asymmetry in DNA methylation between daughter cells may be due to many factors, including RNA-RNA interactions, and RNA-DNA interactions that serve as a signal to trigger de novo DNA methylation. For a review of this RNA-directed DNA Methylation see Theirry Pélissier et al., Heavy de novo methylation at symmetrical and non-symmetrical sites is a hallmark of RNA-directed DNA Methylation, Nucleic Acids Research, 1999, Vol. 27, No. 7.

In both plants and animals, DNA methylation has been identified as a powerful mechanism to regulate gene expression and is thought to play an essential role in a number of cellular processes, such as developmental control, genomic imprinting, and gene silencing. Without being bound by theory, nonsymmetrical methylation of DNA between daughter cells may be partially responsible for the differences between the two classes of cells.

Additionally, the Applicant has discovered that post-mitotic daughter cells tend to be spatially entangled. For example, the cells are often arranged spatially so that each cell type is either directly adjacent to cells, or separated by only one or a few cells, from the other cell class. In this manner, cellular mediators produced by each class of cells may be readily transmitted to cells of the other class. Other means of cellular communication may also be transmitted to cells of the other class.

The Applicant has further discovered that these two classes of post-mitotic daughter cells seem to be temporally entrained, or synchronized. For instance, the Applicant has noticed that if one of the two daughter cells from a mitotic division is killed, the other cell will usually divide and form a new pair of cells or enter apoptosis. In addition, cell pairs tend to apoptose together. It is hypothesized that if live daughter cells are separated, the daughter cells divide to form a new pair of cells.

Irrespective of the theories that explain the reasons for the differences between the two classes of cells, this discovery of the two classes of cells and their different characteristics open vast fields of scientific research. Therefore, it will be appreciated that there is a need in the art for methods to distinguish and sort post-mitotic daughter cells into classes in order to enable scientific research of the binary cellular operating system.

BRIEF SUMMARY OF THE INVENTION

This invention relates to methods for distinguishing and sorting cells. In particular it relates to methods for distinguishing and sorting post-mitotic eukaryotic cells into two general classes according to differences in the cell's DNA, RNA, or proteins associated with the cells' chromatin. In some embodiments, the DNA, RNA, and proteins associated with the cells' chromatin may be labeled using antibodies, radiolabels, or any other identification tool or method, and the cells may be distinguished according to differential identification features. In other embodiments, cellular differences may be identified without the need to label cellular features. Such differences may include, but are not limited to, cellular size, chromatin appearance, cytoplasmic volume, nuclear size, granularity, surface charge, light scattering, etc. In other embodiments, samples of DNA or RNA (of any form) may be taken from the cells and be tested for methylation in certain locations, after which, the cells may be distinguished according to differential methylation. In some embodiments, the distinguished cells may be sorted using virtually any technique, including novel techniques and those currently known in the art.

In some embodiments, the two cell classes may be studied and the cells' proteins, glycoproteins, and RNAs may be identified and sorted into subsets. Information about these subsets may then be used to distinguish and sort the two classes of cells found in similar tissues according to the cells' protein, glycoprotein, and RNA makeup.

In some aspects, the ability to distinguish cells based upon differences in DNA methylation, RNA, and proteins found in the chromatin of the daughter cells, combined with the ability to sort these differentiated cells into two classes, may be used for further research. Some such areas of research may include, but are not limited to, genetic engineering, differential drug treatment, virology, pathology, and so forth.

BRIEF DESCRIPTION OF THE SEVERAL VIEWS OF THE DRAWINGS

In order that the manner of the features, advantages, and benefits of the invention may be obtained and may be readily understood, a more particular description of the invention briefly described above will be rendered by reference to specific embodiments thereof that may be illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 is a light micrograph of a specimen of human skin illustrating differential staining characteristics that demonstrate differential viral infection in one of the two cell types, taken at 1500×.

FIG. 8A shows a specimen of human cartilage cells. FIG. 8B shows a bi-nucleated liver cell. FIG. 8C shows dimensional compression (smear) of insect muscle. FIG. 8D shows a horizontal cut through of uterine tube epithelium. The large cells are secretory cells, and the small cells are ciliated cells. Each image illustrates the differential nuclear features found in cell pairs.

DETAILED DESCRIPTION OF EMBODIMENTS OF THE INVENTION

Figure 2:
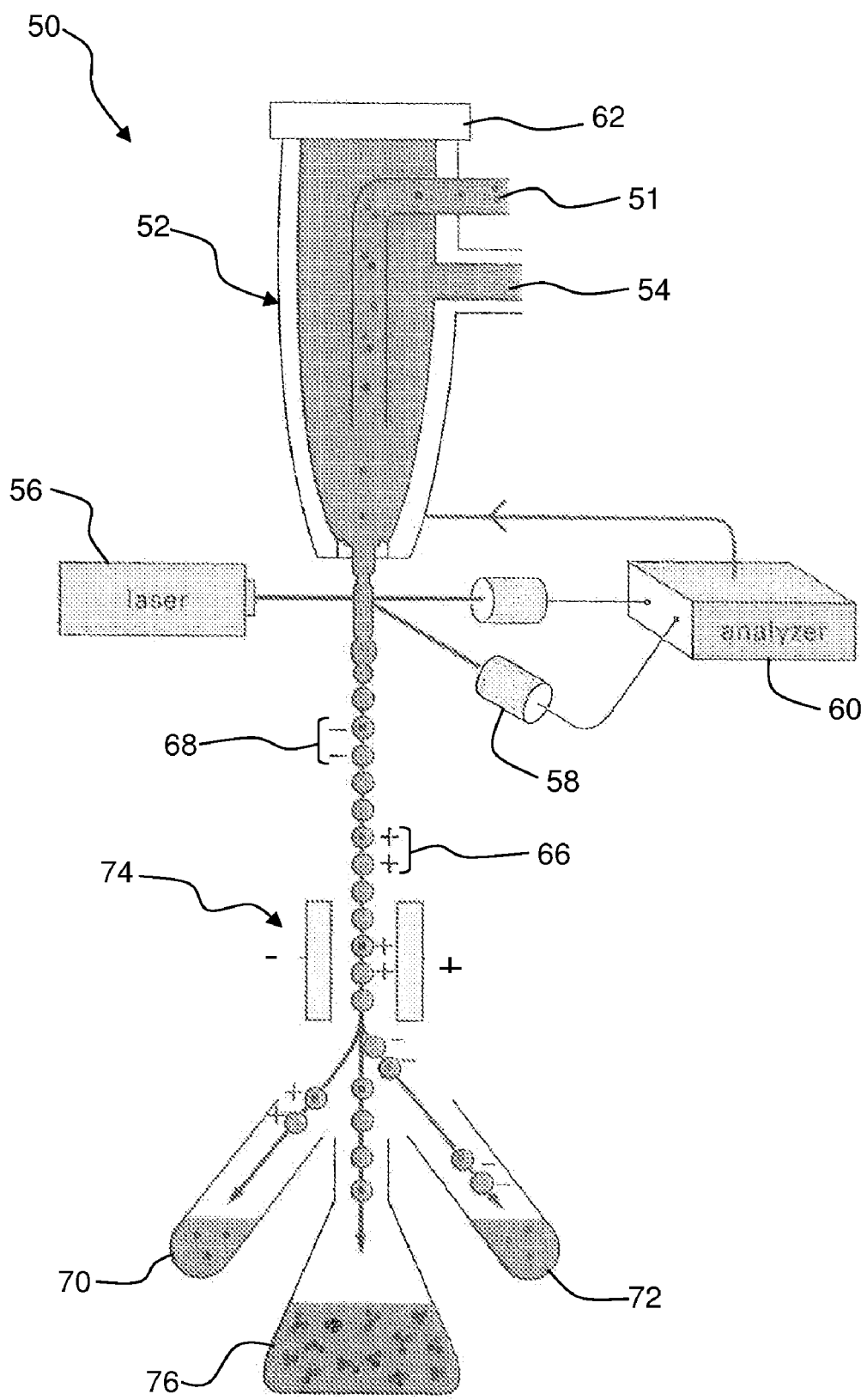
FIG. 2 is a schematic depiction of a flow cytometer.

The following description provides specific details in order to give a thorough understanding of the methods for distinguishing and sorting post-mitotic daughter cells according to differences in the chromatin proteins, RNA, and DNA methylation found in the cells. Nevertheless, the skilled artisan would understand that the described methods can be practiced without employing these specific details. Indeed the methods can be practiced by modifying the described methods and can be used in conjunction with any apparatus and techniques conventionally used. While this invention is described for use with post-mitotic eukaryotic cells, it could be used for any other cell type, including post-meiotic eukaryotic cells, prokaryotic cells, and cells altered in any way. Additionally, the described methods may be used for any purpose, including, but not limited to, research, drug production, genetic engineering, gene therapy, and modification of cellular features.

The above-identified U.S. patent application Ser. No. 11/400,468, discloses several examples of the observable differences in post-mitotic eukaryotic daughter cell pairs, including, but not limited to, differences in nuclear size, chromatin appearance, cytoplasmic volume, and other cytoplasmic differences of the two classes of daughter cells. As previously mentioned, in some aspects, these differences may be due to variations and/or modifications in the proteins found in the cells' chromatin, the numbers of proteins found in the cells' chromatin, differential DNA methylation, differential RNA bound to DNA, etc. between the cells. For example, two daughter cells may vary according to histone alterations in each of the daughter cells' chromatin, according to point/site alterations in the cells' chromatin, according to chromatin protein modifications, according to specific nucleotides that are methylated or unmethlylated, and according to other such differences. Although little is known about the function of cytoplasmic histones, they may also be differentially modified and contribute to the "light" and "dark" cell phenomena. Although they are not a limiting factor in this application, these differences in DNA, RNA, and chromatin proteins (e.g., histones) may influence the cells' role and functions (e.g., protein production, cell structure, cell communication, cell function, etc.). Accordingly, this invention relates to methods for distinguishing daughter cells based upon differences in the daughter cells' DNA, RNA, chromatin proteins, and/or differences in cytoplasmic features. This invention further relates to methods for sorting the differentiated cells into two general classes, class 0 and class 1, which may be used for further research and analysis.

The present invention may utilize any label (including markers, tags, reporters, probes, etc.) or test that may be used to differentially label (including marking, tagging, reporting, probing, etc.) or identify post-mitotic daughter cells according to differences in the cells' chromatin proteins, RNA, methylation of the cells' DNA, or any other differences. These differences may comprise any distinguishable characteristic, including those previously mentioned.

In some embodiments, any known or novel chemical that can be used to differentiate post-mitotic daughter cells into two classes according to differences in the cells' chromatin proteins (e.g., histones) may be utilized. Some examples of suitable chemicals may include dyes or pigments that may provide contrast or visibility to otherwise transparent portions of the cells (e.g., chromatin) or between two cells that are otherwise indistinguishable. In some embodiments, these chemicals may specifically label particular DNA or proteins associated with the cells' DNA and chromatin (e.g., histones). Some examples of such chemicals may include, but are not limited to, ethidium bromide, propidium iodide, SYTOX green, 4,6-diamidino-2-phenylindole (DAPI), and other chemicals that will react and show a distinguishable cellular difference. The cells that may be treated with these chemicals may be alive or dead, and, in some embodiments, they may be fixed or otherwise prepared using any method known in the art.

In other embodiments, radioisotopic labeling may be used to differentially label post-mitotic daughter cells according to differences in the cells' chromatin proteins (e.g., histones), RNA, DNA, etc. In this process, biological compounds can be made using any radioactively labeled molecules, such as P32, I131, S35, C14, Ca45, and H3. Because virtually all biological compounds may be made using radioactively labeled molecules, practically any protein associated with post-mitotic cells' chromatin, proteins, RNA, DNA, etc. may be radiolabeled. For example, the amino acids lysine and/or arginine may be radiolabeled and integrated into some of the cells' histones. The cells may then be distinguished according to the placement and intensity of radioactive emissions. Point mutations in the cells may be used in a similar way to radiolabeling.

In still other embodiments, any known or novel antibody can be used to differentiate post-mitotic daughter cells into two classes according to differences between the cell's chromatin proteins, RNA, or DNA methylation. These antibodies may comprise any type of antibody, including monoclonal or polyclonal antibodies. Further, any number or combination of antibodies may be used to differentially label the cells. For example, in some embodiments, a primary antibody could be applied to the antigen (e.g., a histone or DNA feature) in a single stage. In other embodiments, a secondary antibody may be used to target a species-specific part of the structure of a primary antibody. The use of a secondary antibody may be advantageous because multiple secondary antibodies may bind to a primary antibody and thereby amplify the signal.

Whether the antibodies are used alone, in a single stage, or in conjunction with other antibodies, in multiple stages, the primary and/or secondary antibodies may be directly conjugated with a label. A label may be any chemical group or radioactive atom added to a molecule that is used in order to track material through a reaction or to locate material spatially. In some embodiments, a color or radioactivity may be emitted from the site of an antibody-antigen complex and the emissions may be of varying intensities. Any suitable label may be used help distinguish the cells. Some examples of suitable labels may include, but are not limited to, biotin, Texas red, fluorescein, rhodamine, green florescent protein, red florescent protein, cyan florescent protein, yellow florescent protein, horseradish peroxidase, alkaline phosphatase, peroxidase, ferratin, colloidal gold spheres, gold nano-particles, radiolabels (such as P32, S35, C14, H3, and I125), and the like. These antibody labels may allow a person or an instrument to detect differences between post-mitotic daughter cells according to the presence, location, intensity, etc. of the antibody labels.

In some embodiments, any type of antibody that can be used to distinguish cells according to differences in chromatin proteins may be implemented. Therefore, in some embodiments, any protein(s) associated with cells' chromatin or any other differential feature may serve as an antigen for the labeled antibody(s). Antibodies can be targeted to any protein associated with chromatin, including, but not limited to, those previously mentioned (e.g., H2A, H2B, H3, H4, histone H1, HMG 14, and HMG 17) and modifications of such proteins. In some embodiments, these antibodies may be particularly useful for the differentiation of post-mitotic daughter cells according to differences between the chromatin proteins or any other differential feature in the two classes of cells. In particular, because all histone subunits are highly conserved, antibodies against conserved regions of these proteins may be particularly useful for distinguishing dimorphic classes of cells from multiple organisms. Nevertheless, some examples of suitable antibodies may include, but are not limited to, anti-histone H2A, anti-histone H2B, anti-histone H3, anti-histone H4, anti-histone H1, anti-HMG 14, anti-HMG 17, and antibodies selective to modifications of the histone proteins.

In other embodiments, antibodies may also be targeted to any modified proteins associated with the post-mitotic daughter cells' chromatin (e.g., histones). These modified proteins that serve as antigens may be modified in any way. Some examples of such protein modifications may include phosphorylation and acetylation of the amino acids that form the proteins. Also, the amino acids that form the proteins may be modified at many positions. For example, one of the lysines or arginines on the N-terminus of a histone may be phosphorylated or acetylated. Thus, antibodies may only form a complex and label cells that contain the specific modified residues. Some examples of such antibodies may include, but are not limited to, anti-histone H4 acetylated at lysine 16, anti-histone H4 acetylated at lysine 5, 8, or 12, anti-histone H1 phosphorylated, and other variations of modified histone antibodies.

In some embodiments, post-mitotic daughter cells may be distinguished according to differential methylation of the cells' DNA. These differences may occur at cytosine residues in the cells' DNA and may be found in one class of cells and not in the other. In other words, any gene found in the cells can be tested for differential DNA methylation.

Further, these methylation differences, or asymmetries, in the DNA between two daughter cells may be detected using any known or novel method. In one example of a method for detecting differential DNA methylation, DNA methylation may be determined through the use of methylation-sensitive restriction enzymes that are used in conjunction with their methylation-insensitive isoschizomers (e.g., HpaII and MspI). The digestion may be followed by hybridization with a gene-specific probe, which may be labeled in any known manner. In such instances, differential digestion may provide a quantitative measure of the amount of methylation in the restriction site being examined through techniques such as Southern Blotting.

In another example of a method for distinguishing cells, or identifying cells as belonging to one of the two classes, according to differential DNA methylation, sodium bisulfite may be used to convert unmethylated cytosines to uracil (and then to thymine in subsequent polymerase chain reactions ("PCR")), while leaving methylated cytosines unchanged. This conversion of cytosines to uracil may also be used in bisulfite genomic sequencing, which may allow for examination of each CG or CN dinucleotide with a PCR amplicon. The described conversion may also be used in methylation-polymerase chain reaction ("MS-PCR") or sequencing, which may provide a readout of the presence or absence of methylated alleles in cells, depending on the specificity of the primers used.

In yet another example of a method for detecting differential DNA methylation between cells, a microarray method coupled with linker-PCR may be used for detecting methylation status of multiple genes at once. In this method, a series of synthesized oligonucloetides may be synthesized and purified to match investigated targets. The oligonucleotides may be immobilized on an aldehyde-coated glass slide to create a DNA microarray for detecting methylation status of the desired genes from cell samples.

Regardless of the method used for distinguishing cells according to differential DNA methylation, cells' may be tested for methylation in genes that are only methylated in one class of cells and not the other to determine cell class. For example, DNA extracted from daughter cells may be tested for methylation at one or more desired gene(s), such as, for example, the β-globin gene. Once tested, cells may be identified as belonging to class 0 or class 1, depending on the differential methylation of the desired gene(s).

Similarly, daughter cells that have been treated with any known or novel label (e.g., radiolabel, antibody, etc.) may be identified and distinguished as belonging to one class or the other using any known or novel method, technique, system, or apparatus for distinguishing post-mitotic daughter cells according to differential labeling. In other embodiments, daughter cells may be identified and distinguished without special labeling based upon cellular differences, including, but not limited to, differences in nuclear size, chromatin appearance, cytoplasmic volume, cytoplasmic differences, such as granularity, and light scattering. Some examples of such methods may include, but are not limited to, microscopy, liquid scintillation, radiation sensitive film, a Geiger counter, flow cytometry (as discussed below), near infrared spectrum analysis, Raman spectroscopy, etc.

Some examples of methods for identifying and distinguishing post-mitotic daughter cells according to differential labeling are herein described. For instance, in one example, a conventional light microscope using bright-field, phase contrast, Nomarski, and/or dark-field microscopy may be used to identify cells of the two classes according to the differential marking of labels, such as horseradish peroxidase. In a second example, a microscope with a florescent light (including a confocal microscope) may be used to distinguish the two classes of daughter cells according to differential labeling of the proteins that are associated with the cells' chromatin with a florescent marker, such as fluorescein or rhodamine. In a third example, cells that are differentially marked with labels, such as horseradish peroxidase, the iron-containing protein ferratin, or colloidal gold spheres, may be distinguished according to differential labeling with the use of an electron microscope (e.g., transmission, scanning, and/or cryoelectron). In a fourth example, cells that are differentially labeled with a radiolabel may be placed below a piece of film that is sensitive to radioactivity. After exposure to the film, the location of the radiolabeled cells may correspond to the image on the film. In a fifth example, cells that are labeled with enzymes, such as alkaline phosphatase or peroxidase may be differentiated with biochemical detection techniques, such as an enzyme-linked immunosorbant assay ("ELISA"). In another example, cells that are differentially labeled may be distinguished by an instrument, such as the flow cytometer, described hereinafter. In each of these examples, differential labeling may refer to different marker placement in a cell, different levels of light, color, and/or radiation emissions, and the like.

Figure 1:
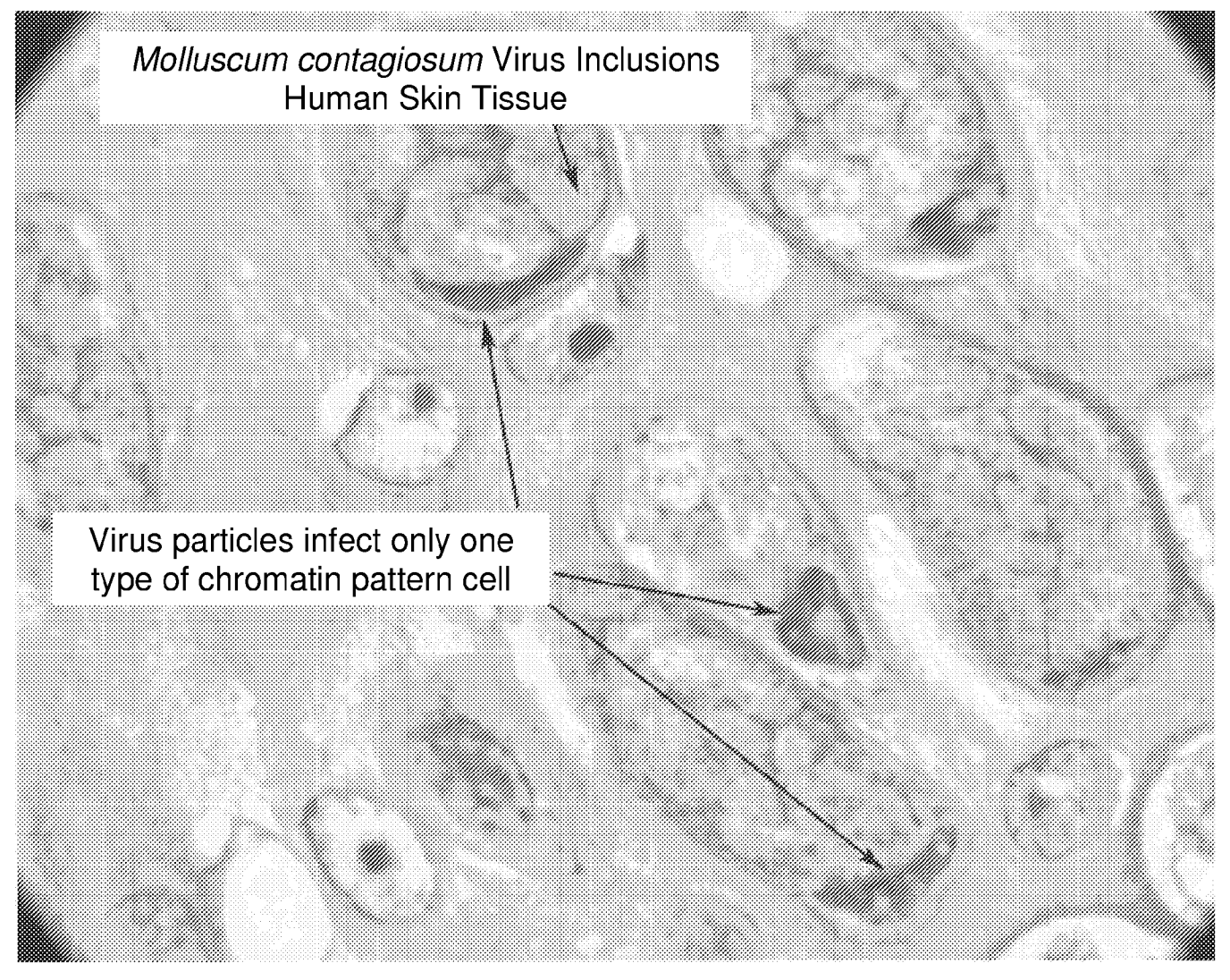

FIG. 1 depicts one example of how post-mitotic daughter cells may be distinguished through the use of a light microscope. FIG. 1 is a specimen of human skin treated with hematoxylin stain and eosin stain illustrating differential staining characteristics that demonstrate differential viral infection in one of the two cell types, taken at 1500×. The resulting image shows that cells labeled in this manner can be distinguished as being light or dark and may thereby be distinguished as belonging to class 0 or class 1.

Figure 8A:
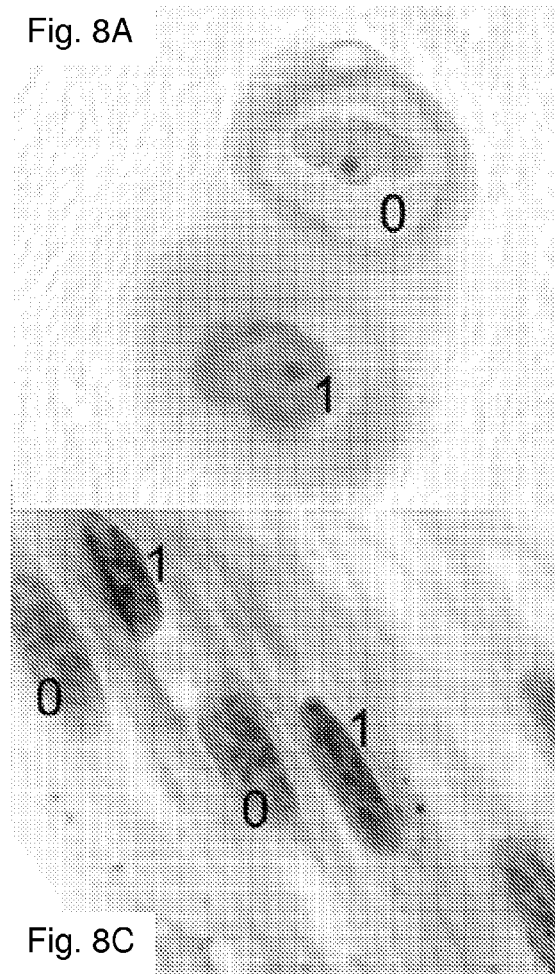
FIGS. 8A-8D are light micrographs showing pairs of cells with differential nuclear features, taken at 1500×.
Figure 8B:
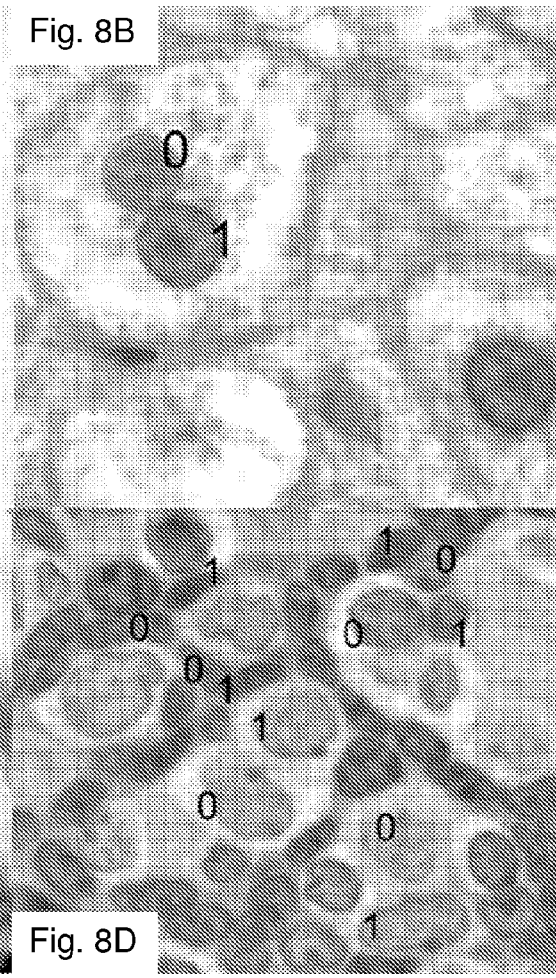
Figure 8C:
Figure 8D:

FIGS. 8A-8D are light micrographs showing pairs of cells with differential nuclear features treated with hematoxylin stain and eosin stain, taken at 1500×. FIG. 8A shows a specimen of human cartilage cells. FIG. 8B shows a bi-nucleated liver cell. FIG. 8C shows dimensional compression (smear) of insect muscle. FIG. 8D shows a horizontal cut through of uterine tube epithelium. The large cells are secretory cells, and the small cells are ciliated cells. Each image illustrates the differential nuclear features found in cell pairs.

Once the post-mitotic daughter cells have been differentiated according to distinguishable differences in the cells chromatin proteins, RNA, DNA methylation, or other distinguishing feature, the cells may be sorted, or separated, using any known or novel techniques, methods, systems, and/or apparatus. For example, the differentiated cells may be sorted mechanically, manually, biochemically, and/or in any other manner. In some embodiments, the techniques, methods, systems, and apparatus for sorting daughter cells into two classes may include flow cytometry, laser capture microdissection ("LCM"), micromanipulation, latex bead agglutination, pipetting, gel electrophoresis, chromatography, affinity assays, and the like.

In some embodiments, flow cytometry may be used to both distinguish and sort post-mitotic cells into two classes according to labeled and/or non-labeled differences of chromatin proteins, RNA, DNA, or other cellular features. Flow cytometry may be used for the measurement of physical and/or chemical characteristics of cells, and, by extension of other biological particles. To accomplish this, flow cytometry may optionally involve labeling specific cells, or in this case, specific cell structures such as proteins (e.g., histones), RNA, or DNA with antibodies that are coupled to a fluorescent dye or other detectable compound. The detected cells may be sorted by using electrical or mechanical means to divert and collect cells with one or more measured characteristcs falling within a range or ranges of values set by the user.

FIG. 2 is a schematic depiction of a flow cytometer 50. As depicted in FIG. 2, a suspension of the labeled post-mitotic daughter cells 51 may be placed in a pressurized hydrodynamic system 52 that is filled with a sheath fluid 54. A stream of cells enveloped in sheath fluid 54 can then be focused and a passed, individually and in single file, through a light beam 56, which may be a lamp or laser. The light emission, absorption, scattering, or florescence of each cell may then be measured and collected by detectors 58 and may be analyzed by one or more analyzers 60. In this way, a flow cytometer may distinguish the class of the post-mitotic daughter cells according to differential cellular features as the cells pass through the laser beam.

In addition to distinguishing differences in the post-mitotic daughter cells, a flow cytometer may also sort the cells. In fact, in some embodiments, a flow cytometer can select 1 cell in a 1000 and sort about 5000 cells per second. To accomplish this, an ultrasonic nozzle vibrator 62 may be used to envelop single cells in droplets of sheath fluid 54 after they have passed through the light beam 56. At the moment each droplet of sheath fluid containing a cell is formed, it may be given a positive charge 66 or negative charge 68, depending on the level of detectable feature as the cells passed through the light beam 56. Once charged, these droplets may be directed, or deflected, to different collectors (70 and 72) by a strong electric field 74. Occasionally, droplets of sheath fluid may contain clumps of cells. These droplets may be detected by their increased light scattering, may be left uncharged, and may be collected in container 76. For example, in the case of the post-mitotic daughter cells, class 0 cells may have a lower level of detectable feature and be sent to a sample collector 70, class 1 may have a higher level of detectable feature and may be sent to a second sample collector 72, and mixtures of the two classes of cells, or anything else, may be sent to the container 76. In some embodiments, the ranges or levels of the detectable feature that may be used to sort the cells into the different containers may be set by the user.

Figure 3A:
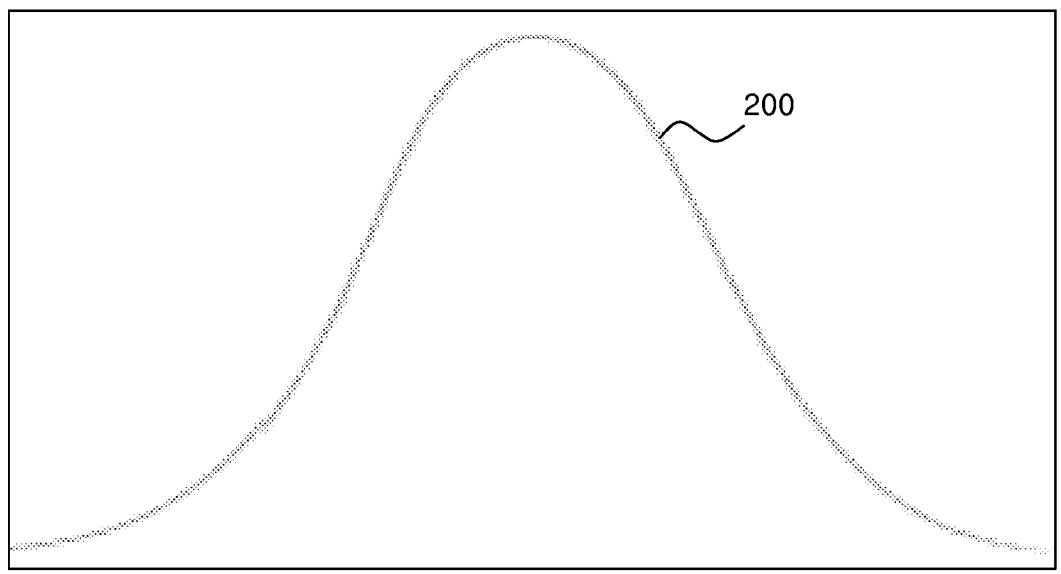
FIG. 3A illustrates a Gaussian curve that represents the sum of two cell populations.
Figure 3B:
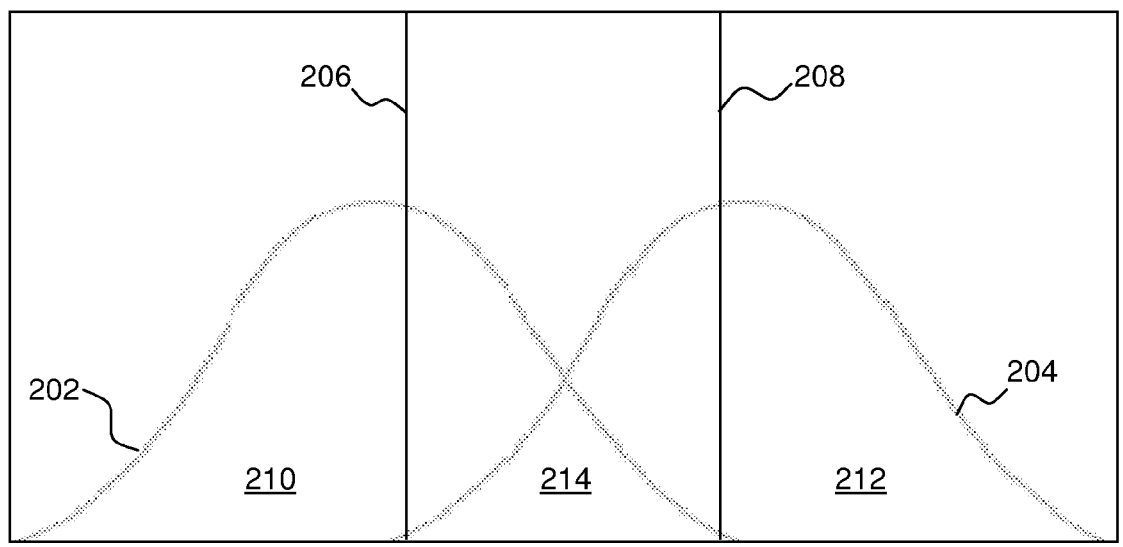
FIG. 3B illustrates two Gaussian curves that represent the sorted distribution of two cell populations.

In the context of flow cytometry, if one knows the cells to be sorted consist of two cell populations, then the sorted distribution curve may be viewed as the summation of two Gaussian distribution curves. The non-overlapping edges of the distribution curves will include separated cells from each class. An illustration of this concept is shown in FIGS. 3A and 3B. FIG. 3A shows a Gaussian curve 200 that represents the sum of two cell populations. What appears to be a simple population of cells is actually a mixed population of two types of cells. FIG. 3B shows two Gaussian curves 202, 204 that represent the sorted distribution of two cell populations. Summating the two curves results in the single curve in FIG. 3A.

By setting gating parameters, represented by lines 206, 208, a flow cytometer can collect three fractions: a nearly homogeneous population of cell type zero 210, a nearly homogeneous population of cell type one 212, and a mixed population 214 of cell types 210 and 212. Each fraction, representing cell type zero 210, cell type one 212, and the mixed population 214 may be analyzed separately with respect to proteome, glycoproteomic, gene expression, etc. The mixed population 214 may be viewed as a wild type control population, as it may demonstrate a different behavior than cell populations 210 and 214.

One or more distinguishing features of each cell class may be used as gating criteria to further separate the sample. The cell populations may be passed through the flow cytometer more than once to enrich the separated cell populations.

Laser capture microdissection ("LCM") is another method that may be used to sort post-mitotic daughter cells once they have been identified as belonging to one class. In this method, a section of tissue containing cells, that may or may not be labeled, is placed on a slide, covered with a piece of special transparent transfer film, and then placed on a microscope. Under the microscope, the thin tissue section may be viewed through the glass slide on which it is mounted. At that point, the operator of the microscope may identify cells according to different characteristics or features. When the cells of choice are in the center of the field of view, the operator may activate a near infrared ("IR") laser diode integral with the microscope optics. A pulsed laser beam is emitted and activates a precise spot on the transfer film immediately above the cells of interest. The size of the targeting pulses may be selected by the operator, as desired. At the precise targeted location, the film may melt and fuse with the underlying cell or cells. Because the laser energy is absorbed by the film, the capture process may not damage the cells. When the film is removed, the chosen cell(s) may be tightly held within the locally expanded polymer, while the rest of the tissue may be left behind. The cells that are connected to the film may retain their morphologic features and thus allow the operator to verify that the correct cells have been procured. In this way, LCM may allow an operator to select cells according to differential labeling and then pool the two classes of samples for further analysis.

Micromanipulation is another method in which post-mitotic daughter cells may be sorted after they have been distinguished. Any known or novel form of micromanipulation can be used to sort the cells. In one example of sorting distinguishable daughter cells using micromanipulation, an operator of a microscope may view cells under a microscope and look for differential labeling of cells' chromatin proteins (e.g., histones), RNA, DNA or other differentially measurable cellular features. After the operator has identified the different cells, the operator may use a micromanipulator, like the CellManipulator® developed by MMI Molecular Machines & Industries Inc, Manchester, N.H., to separate and sort the cells. The CellManipulator may allow an operator to sort cells by using up to ten laser beams to exert exact pressure points at non-biologically destructive frequencies. It functions as optical tweezers to provide contact-free manipulation of microscopic particles. In addition to this device, any other micromanipulator could be used.

In another example of sorting daughter cells into two classes through micromanipulation, cells may be manually sorted with any conventional instrument or means. For example, an operator of a microscope may identify the two classes of cells according to differential labeling or other differential cellular features. After identifying cells of each class, the operator may sort the cells with a microscopic blade, a baby hair, a fine wire.

In yet another example of micromanipulation, an operator of a microscope could use the microscope to distinguish cells (i.e., into class 0 or class 1) and use a micropipette, capillary tube, or charged particles to remove the desired cells from the sample. For example, an operator of a fluorescent microscope may look at a diluted sample of ova through a microscope and determine which cells fall into class 0 and which fall into class 1. As the operator determines the status of each cell, the operator may use a micropipette connected to a micromanipulator to remove and sort the desired cells.

Figure 4:
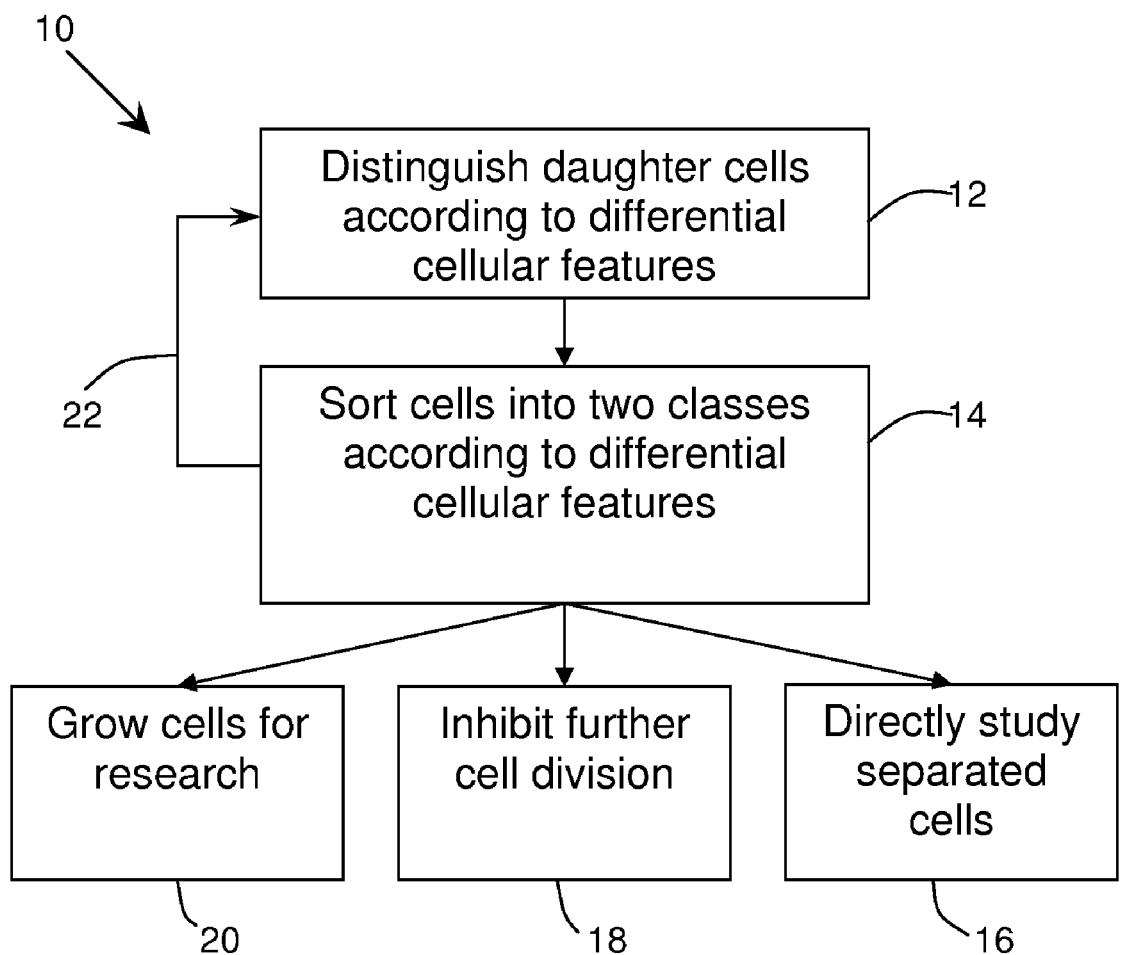
FIG. 4 is a flow chart of a typical embodiment of one method for identifying and sorting cells into classes.

Although the methods for sorting post-mitotic daughter cells may be completed in any desired manner or by any desired means, one example of an embodiment of a typical method 10 is illustrated in FIG. 4. This Figure is provided as an exemplary embodiment, meaning that variations are possible and that the steps need not be followed sequentially. In an initial step 12, cells are distinguished according to differential cellular features. In some cases, cellular features may be more easily distinguished by using a molecular label (including markers, tags, reporters, probes, etc.) or test to differentially label or identify post-mitotic daughter cells according to differences in the cells' chromatin proteins, RNA, methylation of the cells' DNA, or any other differences. Post-mitotic daughter cells may be differentially labeled or tested using any known or novel method (e.g., with antibodies, stains, radiolabels, in situ probes, microarray technology, methylation-sensitive digests, etc.). Some cellular features may be distinguished without labeling, such as cellular size, chromatin appearance, cytoplasmic volume, nuclear size, granularity, surface charge, light scattering, etc.

The differential cellular features will often be distinguished mechanically, manually, or chemically. For example, the cells may be passed through a flow cytometer and be distinguished according to detectable cellular differences of the two classes of cells, such as differential fluorescence, cytoplasmic volume, light scattering, etc. In another example, an operator of a microscope may manually observe the cells through a microscope and under florescent light in order to determine which cells fall into the two classes according to the differential labeling.

Once the cells have been distinguished, the cells are sorted into classes (e.g., class 0 and class 1), as shown at step 14. A mixture of class 0 and class 1 cells may be obtained and may provide a wild type control as to behavior of the mixture. As mentioned, this can be done using any method, including, but not limited to, flow cytometry, LCM, micromanipulation, etc. No matter the method used to sort the cells, once a uniform population of cells has been obtained it can be used directly for research or biochemical analysis, as shown at step 16. The sorted cells may be treated to prevent cell division in step 18, and further studied to observe the behavior of sorted cells under controlled conditions. Alternatively, as shown at 20, the sorted cells may provide a suitable starting material for cell culture, allowing the behavior of the two types of cells to be studied under the strictly defined growth conditions.

In some cases it will be desirable to subset the sorted cells based upon other identifiable differences between daughter cells. In this case, sorted cells may be processed again according to steps 12 and 14. These steps may be repeated as shown by arrow 22.

After post-mitotic daughter cells from specific tissue in an organism have been distinguished and sorted, those cells may be studied and information and characteristics of the cells may be used to separate similar cells in the future, without necessarily following the steps illustrated in FIG. 4. Although two post-mitotic daughter cells may contain identical DNA, the applicant has found that the two classes of cells' DNA may be packaged differently, as previously noted. It is commonly understood that the manner in which a region of the genome is packaged into chromatin in a particular cell may influence the activity of the genes the region contains. Further, as mentioned, DNA methylation tends to play an important role in cellular process, including gene silencing. As a result of these two factors, as well as others, it is theorized that two daughter cells that share copies of the same DNA have differential RNA expression patterns, proteomes, and glycoproteomes.

RNA from the two cell types may be collected and applied to RNA microarray analysis in order to determine the gene expression patterns of the two cell types. If one cell type is making more and different RNAs, it is also likely (though not definitely) making more and different proteins. RNAs may be responsible for signaling in the cell that can lead to increased or decreased expression of other genes. Further, functional proteomics may be used to analyze the protein production and interactions of the two cell types. Proteins from each of the two cell types may be collected and applied to protein microarrays in order to identify the proteins present and quantify the amount of protein in the sample and the interactions between proteins. Capture arrays that quantify interactions can be used to recreate a protein interaction network for each of the two cell types. Unique proteins and protein interactions from either cell type may lead to the discovery of specific entities that, at least partially, determine cell type. These unique proteins may be used in recombinatorial cloning experiments wherein one cell type is transformed into to the other cell type by increasing or decreasing the expression levels of the unique proteins. Glycoprotein composition can be analyzed using lectin based glycoprotein arrays that give a profile of glycoprotein content of a cell. The glycoproteins could also be captured by lectins, purified, and analyzed by mass spec or various chromatographic methods to identify any glycoproteins not included in the glycoprotein array. Hence, in some embodiments, once the two classes of post-mitotic daughter cells have been distinguished and sorted using the methods similar to those previously mentioned, a study of the cell's proteomes and glycoproteomes may reveal RNAs, proteins, and glycoproteins that are unique to each class of cells. With this knowledge, post-mitotic daughter cells from similar tissues can be easily distinguished and sorted using virtually any known means for sorting cells according to differences in the cells' proteins and/or glycoproteins.

For example, post-mitotic daughter cells that have been distinguished and sorted through any method similar to that shown in FIG. 4 can be fractionated and used to determine the classes of cells' proteomic, glycoproteomic, and RNA subsets. Any conventional protein, glycoprotein, and/or RNA separation and identification process may be used to determine the proteomic, glycoproteomic, and RNA subsets of the different classes of daughter cells. Some suitable methods for protein separation may include conventional methods, such as sodium dodecyl sulfate polyacrylamide-gel electrophoresis ("SDS-PAGE"), two dimensional PAGE, Western Blotting, chromatography (e.g., ion-exchange, gel-filtration, and affinity), high performance liquid chromatography, mass spectroscopy, centrifugation, microarray technology, and reverse transcriptase polymerase chain reaction ("RT-PCR").

In some embodiments, chromatography may be used, for example, to sort the two classes of cells once the subsets of the cells' proteomes and glycoproteomes have been established. Virtually any form of chromatography may used to sort the cells into the two classes according to differential labeling. Some suitable forms of chromatography may include, for example, column chromatography. Some examples of column chromatography may include ion-exchange chromatography, gel-filtration chromatography, affinity chromatography, and high-performance liquid chromatography ("HPLC"). One example of sorting cells into two classes according to differential proteins or glycoproteins with chromatography may include coupling an enzyme substrate, which is targeted to proteins that are unique to each class of cells, to an inert matrix (e.g., polysaccharide beads) to produce an affinity column. The enzyme that operates on that substrate may be retained, along with the cells associated with the enzyme, by the matrix and may then be eluted (washed out) in nearly a pure form. Thus one class of daughter cell may be collected. In some embodiments, the elution may be passed through a second column, which includes an enzyme substrate that is only found on the second class of cells. In this way both classes of cells may be collected.

Figure 5:
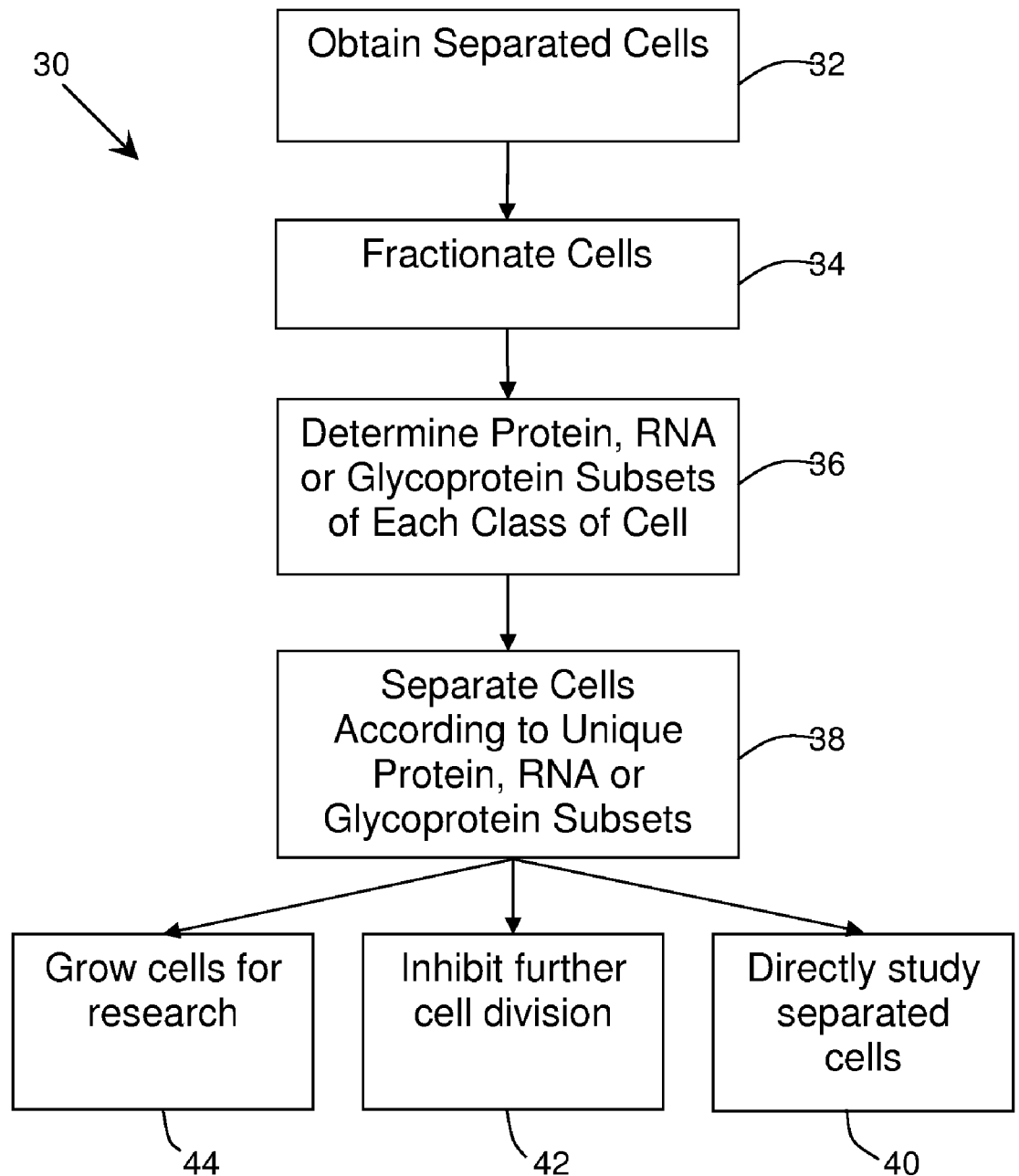
FIG. 5 is a flow chart of another typical embodiment of one method for identifying and sorting cells into classes.
Figure 6:
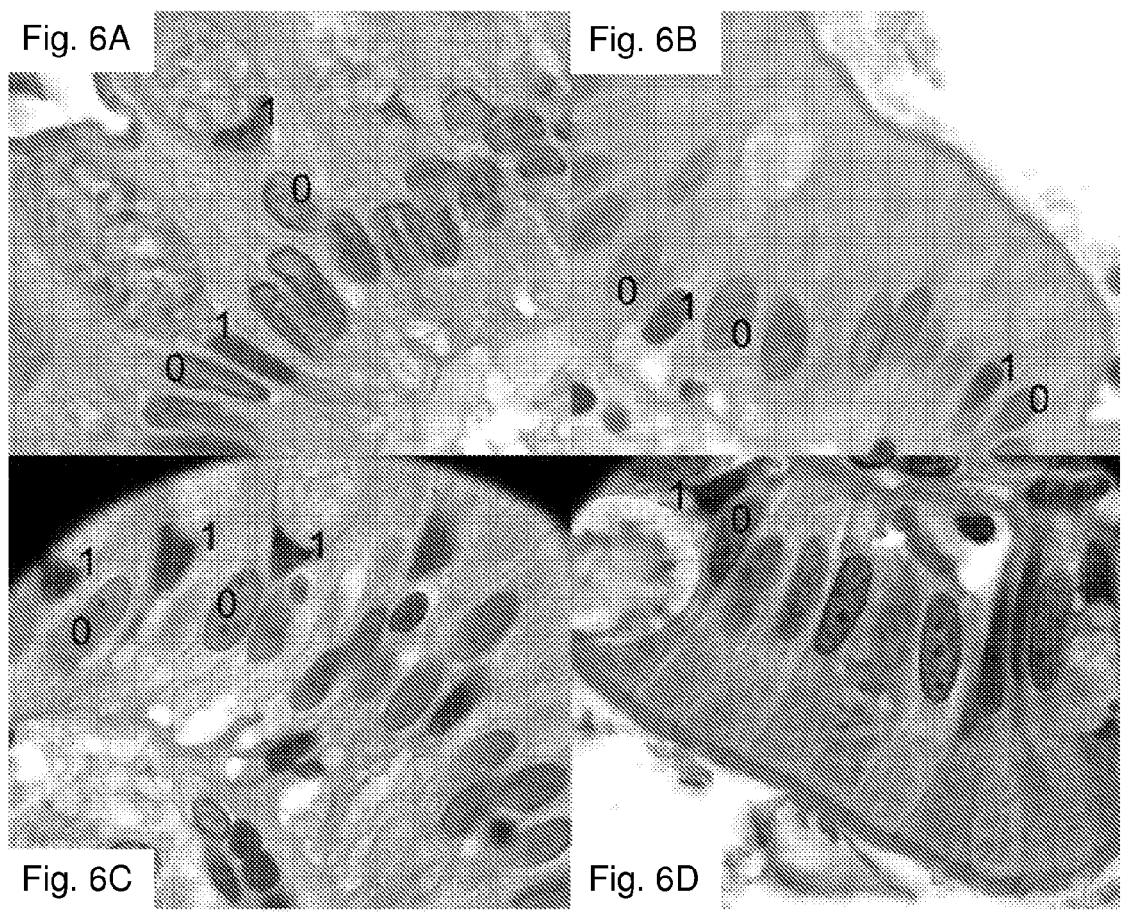
FIGS. 6A-6D are light micrographs of specimens of human gastrointestinal cells showing the two types of daughter cells where type 1 is a secretory cell and has very compact chromatin and type 0 is a water absorbing cell with more diffuse chromatin features, taken at about 2000×.

FIG. 5 illustrates a method 30 to distinguish and sort post-mitotic daughter cells according to differences in the cell's RNA, protein, and glycoprotein subsets. Step 32 of FIG. 5 refers to cells obtained by sorting dimorphic daughter cells, as shown in FIG. 4. Namely, that a group of cells may be distinguished and sorted according to differential cellular features. Once distinguished, the cells may be sorted, as discussed above, and the cells may be collected according to steps 16, 18, and 20 of FIG. 4.

Next, at step 34 in FIG. 5, the sorted classes of cells may be fractionated and identified using any known method (e.g., SDS-PAGE electrophoresis, chromatography, etc.). At 36, the proteins, RNA, and glycoproteins of the separate classes of cells may then be compared, and the proteins and glycoproteins that are unique to each class of cells may be identified using any conventional method (e.g., mass spectroscopy). These unique proteins, RNA, and glycoproteins, or subsets, may then be used in the future for the identification and sorting of the post-mitotic daughter cells of similar tissues in a similar organism. For example, step 38 illustrates that post-mitotic daughter cells may be sorted using any method known in the art. In one embodiment, antibodies may be made that bind to proteins, RNA or glycoproteins that are found on one cell class and not on the other. These class specific antibodies may be coupled to various matrices, such as collagen, polysaccharide beads, or plastic, to form an affinity surface to which only cells recognized by the antibodies will adhere. The bound cells may then be recovered by gentle shaking, by treatment with trypsin to digest the proteins that mediate the adhesion, or, in the case of a digestible matrix (such as collagen), by degrading the matrix itself with enzymes (such as collagenase). In this manner, post-mitotic daughter cells may be sorted according to differences in proteins and/or glycoproteins, and not only by directly differentially labeling the chromatin proteins and/or testing for asymmetric DNA methylation for each tested cell. Once again, the distinguished and sorted cells may be directly studied once sorted, as depicted at step 40, may be treated to prevent cell division in step 42, and further studied to observe the behavior of sorted cells under controlled conditions, or alternatively, as shown at step 44, the sorted cells may provide a suitable starting material for cell culture, allowing the behavior of the two types of cells to be studied under the strictly defined growth conditions.

These methods for distinguishing and sorting post-mitotic daughter cells according to differences in the cells' chromatin proteins (e.g., histones), RNA, differential DNA methylation, or other cellular features have numerous utilities and represent a dramatic advance in science. Because this invention is substantially related to a basic building block of life, the cell, this invention may influence every facet of biology and medicine, as currently understood. Some applications for these methods may be found in areas including, but not limited to, genetic engineering, gene therapy, differential drug treatment, in vitro fertilization, viral operation research, cancer research, prion research, binary operation of cells, differential drug treatment research, proteomics, stem cell research, glycoproteomics, pathological research, bioinformatics, and basic research.

For example, FIG. 1 not only shows differential staining in post-mitotic human skin cells, as discussed above, but that Figure also shows differential infection of the cells by a virus, *Molluscum contagiosum*. This differential infection is apparent from the presence of viral inclusions in cells that have the class 1 pattern of chromatin staining, whereas the cells with the class 0 pattern of chromatin staining are relatively free from viral inclusions. These methods for sorting post-mitotic daughter cells may provide an opportunity to study the differences between the proteins, glycoproteins, and RNA of the two classes of cells. In this manner, researchers may be able to determine how the one class of cells can block viruses and what can be done to help all cells block certain viruses. With this information, the subjects of virology and pathology may be substantially advanced, and researchers may be able to determine improved methods for preventing or retarding viral infections in virtually all organisms, including humans.

Additionally, information about the differences in proteins and glycoproteins, discovered by distinguishing and sorting the cells into the two classes, may lead to advances in drug treatment. For example, certain ailments, such as cancer, may need to be treated with two types of drugs, one that affects cells from each class. Advances in differential drug treatment that are based upon information gained through the identification and sorting of post-mitotic daughter cells may play an integral role in the treatment of many diseases which are found to affect only one class of cells or which affect each class differently.

In some embodiments, these methods for sorting post-mitotic daughter cells into two classes may be useful in genetic engineering. For example, it is currently understood that one gene sets off development for each ventricle of the heart and that much of the sculpting of the heart is done by post-mitotic daughter cells. Although two post-mitotic cells may be the result of one stem cell that divided, and both cells may share identical DNA, one of the post-mitotic daughter cells may become a red blood cell, while the other daughter cell becomes a muscle cell in the heart. The described methods may be used to determine what causes one daughter cell to be a blood cell and the other to be a muscle cell. With this information, researchers may discover ways to replace necrotic heart tissue, or any other tissue, and sculpt a dying or malformed organ through the use of post-mitotic daughter cells and knowledge of their two classes.

In a similar manner, the applicant has observed, through many observations of gastrointestinal cells, the visible differentiation of daughter cells. One daughter cell differentiates to absorb water and the other daughter cell differentiates to secrete mucous, as shown in FIGS. 6A-6D. Type 1 daughter cells are secretory cells having very compact chromatin. Type 0 daughter cells are water absorbing cells with more diffuse chromatin features. The same nuclear features can be appreciated in cell cultures and touch preparations of fresh tissue.

Figure 7:
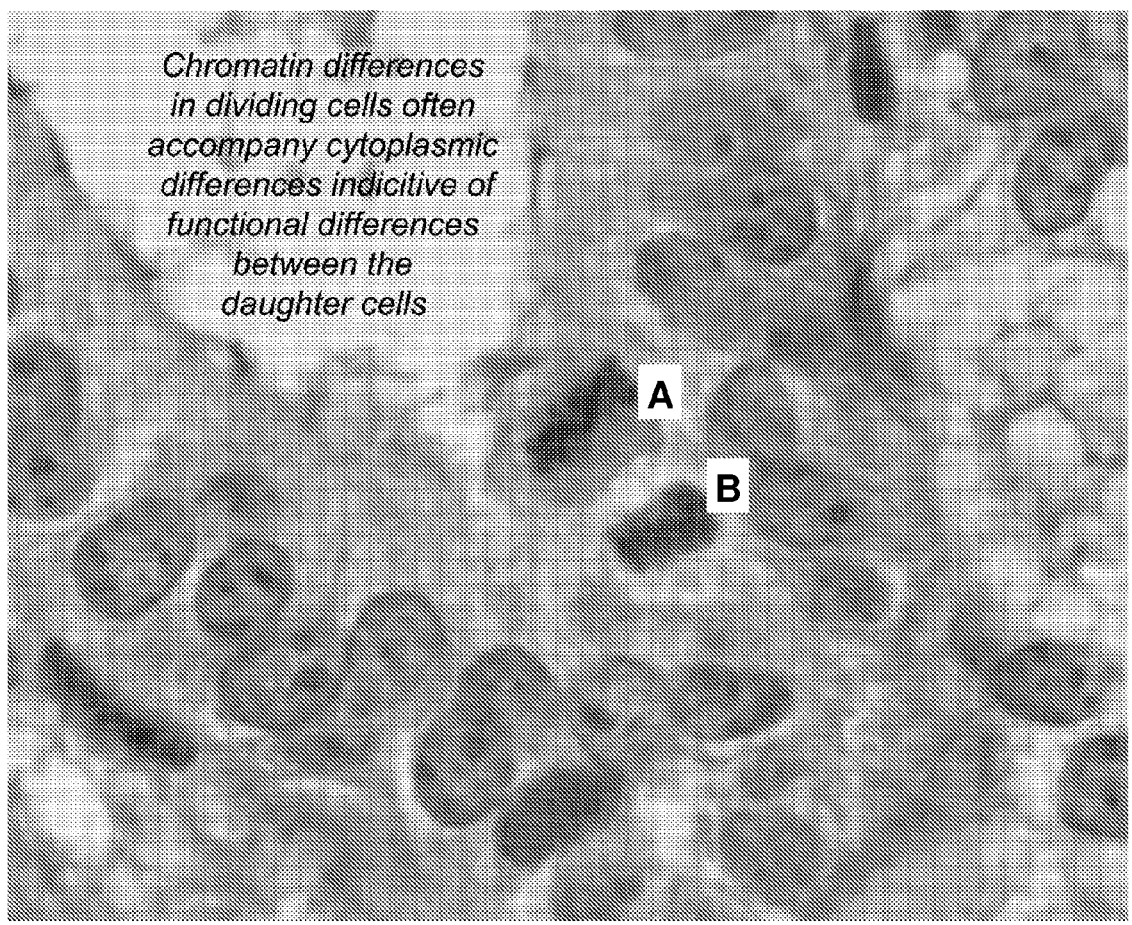
FIG. 7 is a light micrograph of a specimen of colonic epithelial cells illustrating that chromatin differences in dividing cells often accompany cytoplasmic differences indicative of functional differences between the daughter cells, taken at about 2000×.

FIG. 7 shows a light micrograph of a specimen of colonic epithelial cells illustrating that chromatin differences in dividing cells often accompany cytoplasmic differences indicative of functional differences between the daughter cells, taken at about 2400×. The figure shows two cells at the end of telophase, one having very dense cytoplasmic staining (labeled "A") and one having much lighter cytoplasm (labeled "B"). The cell having the denser cytoplasm will develop into a mucous secreting cell while the cell with lighter cytoplasm will become a water absorbing cell.

Besides the aforementioned specific and substantial utilities, as well as many others, these methods for sorting post-mitotic daughter cells may be used for basic research. In this way, these methods may be used to advance many fields, including but not limited to, cytology, microbiology, immunology, cardiology, neurology, oncology, hematology, osteology, pathology, and histology. In one example of how these methods may benefit basic research, it has been noted that post-mitotic daughter cells seem to temporally entrained and spatially entangled. In fact, when one of two post-mitotic daughter cells dies, the remaining cell will usually divide to form a new pair of cells or enter apoptosis. Information about communication between post-mitotic daughter cells may therefore be useful to inhibit or promote cell division and/or apoptosis. Information such as this may aid in the basic research of virtually any living organism. It may provide useful information regarding genetic control circuits and understanding the binary nature of cells.

The present invention may be embodied in other specific forms without departing from its methods, structures, or essential characteristics as broadly described herein and claimed hereinafter. The described embodiments are to be considered in all respects only as illustrative and not restrictive. The scope of the invention is, therefore, indicated by the appended claims, rather than by the foregoing description. All changes that come within the meaning and range of equivalency of the claims are to be embraced within their scope.

The invention claimed is:

1. A method for subsetting the proteome, glycoproteome, or RNA of dimorphic daughter cells from a mitotic cellular division, comprising:
   distinguishing the dimorphic daughter cells from a mitotic cellular division according to differential cellular features present in the daughter cells;
   physically sorting the cells into at least two classes according to the differential cellular features;
   differentially detecting proteins, glycoproteins, or RNA present in each class of cell;
   comparing the proteins, glycoproteins, or RNA present in the classes of cells; and
   identifying proteins, glycoproteins, or RNA that are unique to each class.

2. The method for subsetting the proteome, glycoproteome, or RNA of dimorphic daughter cells of claim 1, wherein the differential cellular features comprise differences in chromatin proteins associated with the cells' chromatin.

3. The method for subsetting the proteome, glycoproteome, or RNA of dimorphic daughter cells of claim 1, wherein the differential cellular features comprise differences in chromatin glycoproteins.

4. The method for subsetting the proteome, glycoproteome, or RNA of dimorphic daughter cells of claim 1, wherein the differential cellular features comprise differential DNA methylation.

5. The method for subsetting the proteome, glycoproteome, or RNA of dimorphic daughter cells of claim 4, wherein the differential DNA methylation is at CpG sites.

6. The method for subsetting the proteome, glycoproteome, or RNA of dimorphic daughter cells of claim 4, wherein the differential DNA methylation is at CpN sites.

7. The method for subsetting the proteome, glycoproteome, or RNA of dimorphic daughter cells of claim 4, wherein the differential DNA methylation is at CpNpG sites.

8. The method for subsetting the proteome, glycoproteome, or RNA of dimorphic daughter cells of claim 1, wherein the differential cellular features comprise differential RNA.

9. The method for subsetting the proteome, glycoproteome, or RNA of dimorphic daughter cells of claim 1, wherein the differential cellular features comprise cellular size, chromatin appearance, cytoplasmic volume, nuclear size, granularity, surface charge, or light scattering.

10. The method for subsetting the proteome, glycoproteome, or RNA of dimorphic daughter cells of claim 1, further comprising using the differences in proteins, glycoproteins, or RNA of the two classes of cells to sort post-mitotic daughter cells of same tissue.

11. The method for subsetting the proteome, glycoproteome, or RNA of dimorphic daughter cells of claim 1, further comprising the step of providing the sorted daughter cells of a first class as starting material for a first cell culture and growing the first cell culture.

12. The method of sorting dimorphic daughter cells of claim 11, further comprising the step of providing the sorted daughter cells of a second class as starting material for a second cell culture and growing the second cell culture.

13. The second cell culture according to the method of claim 12.

14. The first cell culture according to the method of claim 11.

15. Isolated dimorphic daughter cells sorted as Class 0 cells and Class 1 cells according to the method of claim 1.

16. Isolated dimorphic daughter cells sorted as Class 0 cells and Class 1 cells according to the method of claim 4.

* * * * *